(12) United States Patent
Yano et al.

(10) Patent No.: US 8,236,286 B2
(45) Date of Patent: Aug. 7, 2012

(54) LIQUID COMPOSITIONS FOR THE ORAL CAVITY

(75) Inventors: Yoshitaka Yano, Tokyo (JP); Shigeto Kayane, Tokyo (JP); Takahisa Yamashiro, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/576,858

(22) PCT Filed: Oct. 20, 2005

(86) PCT No.: PCT/JP2005/019289
§ 371 (c)(1),
(2), (4) Date: Apr. 6, 2007

(87) PCT Pub. No.: WO2006/043621
PCT Pub. Date: Apr. 27, 2006

(65) Prior Publication Data
US 2008/0038210 A1    Feb. 14, 2008

(30) Foreign Application Priority Data

Oct. 20, 2004   (JP) ................. 2004-306043
Oct. 20, 2004   (JP) ................. 2004-306044

(51) Int. Cl.
*A61K 8/00*    (2006.01)
*A61K 8/46*    (2006.01)

(52) U.S. Cl. ........................... 424/49; 424/57
(58) Field of Classification Search .............. 424/49, 424/57
See application file for complete search history.

(56) References Cited

U.S. PATENT DOCUMENTS

| | | | |
|---|---|---|---|
| 4,323,551 A * | 4/1982 | Parran, Jr. ................ | 424/54 |
| 4,865,839 A * | 9/1989 | Saso ........................ | 424/54 |
| 4,913,895 A * | 4/1990 | Miyake et al. ............ | 424/57 |
| 5,626,837 A | 5/1997 | Shimada et al. | |
| 6,607,736 B2 * | 8/2003 | Ohmori et al. ........... | 424/401 |
| 7,462,604 B2 | 12/2008 | Kaneda et al. | |
| 2007/0116657 A1 | 5/2007 | Kaneda et al. | |

FOREIGN PATENT DOCUMENTS

| | | |
|---|---|---|
| EP | 0 009 325 A1 | 4/1980 |
| EP | A-1 532 971 | 5/2005 |
| JP | 55-34098 A | 3/1980 |
| JP | 60-204710 A | 10/1985 |
| JP | A-04-202121 | 7/1992 |
| JP | 06-211636 A | 8/1994 |
| JP | A-07-101842 | 4/1995 |
| JP | 07-126131 A | 5/1995 |
| JP | 11-035436 A | 2/1999 |
| JP | 11-071252 | 3/1999 |
| JP | 11-071252 A | 3/1999 |
| JP | 2000-154127 A | 6/2000 |
| JP | 2000-247851 A | 9/2000 |
| JP | 2000-256153 A | 9/2000 |
| JP | 2000-281545 A | 10/2000 |
| JP | A-2000-344641 | 12/2000 |
| JP | 2001-089383 A | 4/2001 |
| JP | 2001-220336 A | 8/2001 |
| JP | 2001-302478 A | 10/2001 |
| JP | 2001-348596 A | 12/2001 |
| JP | 2005-263753 A | 9/2005 |
| JP | 2005-289917 A | 10/2005 |
| WO | WO 01/12229 * | 2/2001 |
| WO | WO 03/103618 A | 12/2003 |
| WO | WO 2004/019800 A2 | 3/2004 |
| WO | WO 2005/030152 A | 4/2005 |

OTHER PUBLICATIONS

English translation of Detailed Description and Claims for JP-2001-348596; 2001.*
English translation of Detailed Description for JP-11-71252; 2001.*
English translation of Detailed Description for JP-11-71252; 1999. (Previously submitted with Apr. 15, 2009 Office action).*
International Search Report for International Application No. PCT/JP2005/019289, Japanese Patent Office, mailed Feb. 7, 2006.
Patent Abstracts of Japan, translated abstract of Publication No. JP 2005-289917 A, Dentifrice Composition, published Oct. 20, 2005, (listed on accompanying PTO/SB/08A as document FP1).
Patent Abstracts of Japan, translated abstract of Publication No. JP 2005-263753 A, Liquid Composition for Oral Cavity, published Sep. 29, 2005, (listed on accompanying PTO/SB/08A as document FP2).
Patent Abstracts of Japan, translated abstract of Publication No. JP 2001-302478 A, Liquid Composition for Oral Cavity, published Oct. 31, 2001, (listed on accompanying PTO/SB/08A as document FP3).

(Continued)

*Primary Examiner* — Frederick Krass
*Assistant Examiner* — Chris Simmons
(74) *Attorney, Agent, or Firm* — Sterne, Kessler, Goldstein & Fox P.L.L.C.

(57) ABSTRACT

The present invention relates to a liquid composition for the oral cavity, which contains the following components (A), (B), (C) and (D):

(A) an oil-soluble flavor,
(B) a cationic bactericide,
(C) a sugar fatty acid ester, and
(D) one or more compounds selected from the group consisting of polyglycerol fatty acid esters, polyoxyethylene hydrogenated castor oils, and sorbitan fatty acid esters.

The present invention also pertains to a liquid composition for the oral cavity, which contains the following components (A), (B), (E) and (F):

(A) an oil-soluble flavor,
(B) a cationic bactericide,
(E) a polyphosphoric acid or salt thereof, and
(F) a polyglycerol fatty acid ester.

The liquid composition for the oral cavity according to the present invention is excellent in the adsorption of the bactericide to teeth and the like, barely causes unpleasant odor, and is excellent in stability.

23 Claims, 2 Drawing Sheets

OTHER PUBLICATIONS

Patent Abstracts of Japan, translated abstract of Publication No. JP 2001-220336 A, Composition for Oral Cavity, published Aug. 14, 2001, (listed on accompanying PTO/SB/08A as document FP4).

Patent Abstracts of Japan, translated abstract of Publication No. JP 2001-089383 A, Composition for Oral Cavity and Ophthalmology, published Apr. 3, 2001, (listed on accompanying PTO/SB/08A as document FP5).

Patent Abstracts of Japan, translated abstract of Publication No. JP 2000-281545 A, Composition for Oral Cavity, published Oct. 10, 2000, (listed on accompanying PTO/SB/08A as document FP6).

Patent Abstracts of Japan, translated abstract of Publication No. JP 2000-256153 A, Oral Composition, published on Sep. 19, 2000, (listed on accompanying PTO/SB/08A as document FP7).

Patent Abstracts of Japan, translated abstract of Publication No. JP 2000-247851 A, Coating Agent for Controlling Coloration, published on Sep. 12, 2000, (listed on accompanying PTO/SB/08A as document FP8).

Patent Abstracts of Japan, translated abstract of Publication No. JP 2000-154127 A, Composition for Oral Cavity, published Jun. 6, 2000, (listed on accompanying PTO/SB/08A as document FP9).

Patent Abstracts of Japan, translated abstract of Publication No. JP 11-071252 A, Composition for Oral Cavity, published Mar. 16, 1999, (listed on accompanying PTO/SB/08A as document FP10).

Patent Abstracts of Japan, translated abstract of Publication No. JP 11-035436 A, Composition for Oral Cavity, published Feb. 9, 1999, (listed on accompanying PTO/SB/08A as document FP11).

Patent Abstracts of Japan, translated abstract of Publication No. JP 07-126131 A, Oral Cavity Composition, published May 16, 1995, (listed on accompanying PTO/SB/08A as document FP12).

Patent Abstracts of Japan, translated abstract of Publication No. JP 06-211636 A, Composition for Oral Cavity Application, published Aug. 2, 1994, (listed on accompanying PTO/SB/08A as document FP13).

Patent Abstracts of Japan, translated abstract of Publication No. JP 60-204710 A, Composition for Oral Cavity, published Oct. 16, 1985, (listed on accompanying PTO/SB/08A as document FP14).

Extended European Search Report for corresponding EPO application No. 05795478.6-2108, mailed Feb. 3, 2009, from the European Patent Office, Munich, Germany.

Patent Abstracts of Japan, English language abstract of No. JP 2001 348596 A, Detergent Composition, published Dec. 1, 2001, (listed on accompanying PTO/SB/08A as document FP18).

Office action from the European Patent Office for EP Appl. No. 05 795 478.6-2108, mailed Dec. 15, 2009 from the European Patent Office, Munich, Germany.

Japanese Office action for JP Patent Appl. No. 2005-304313, mailed Jan. 5, 2011.

Dialog File 351: Derwent World Patents Index, Accession No. 6057858, English language abstract and patent family for JP 4202121A, Jul. 22, 1992.

Dialog File 351: Derwent World Patents Index, Accession No. 7147358, English language abstract and patent family for JP 7-101842, Apr. 18, 1995.

* cited by examiner

[FIG. 1]
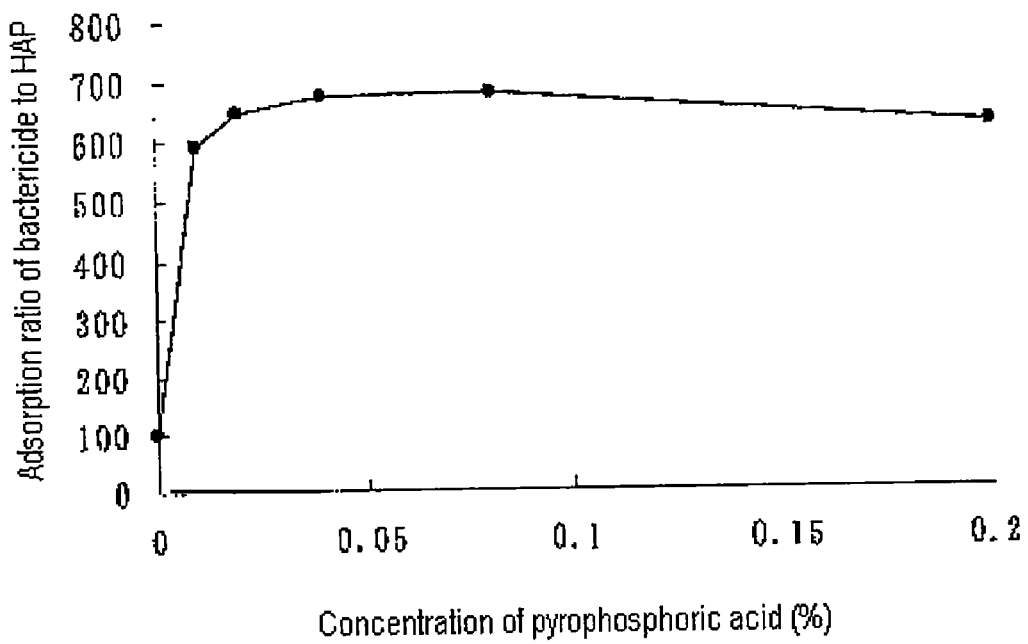
[FIG. 2]
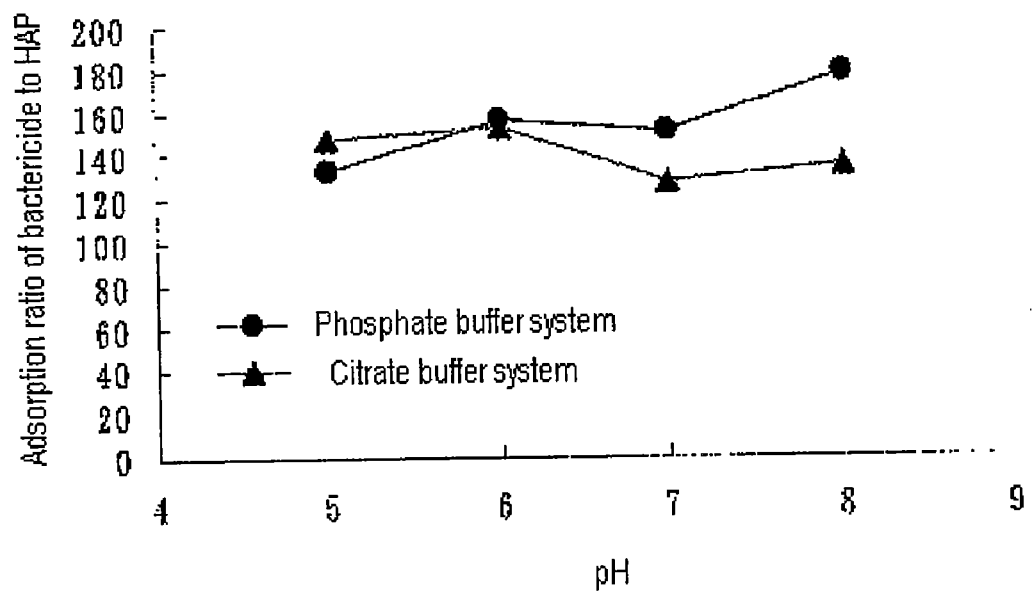

[FIG. 3]
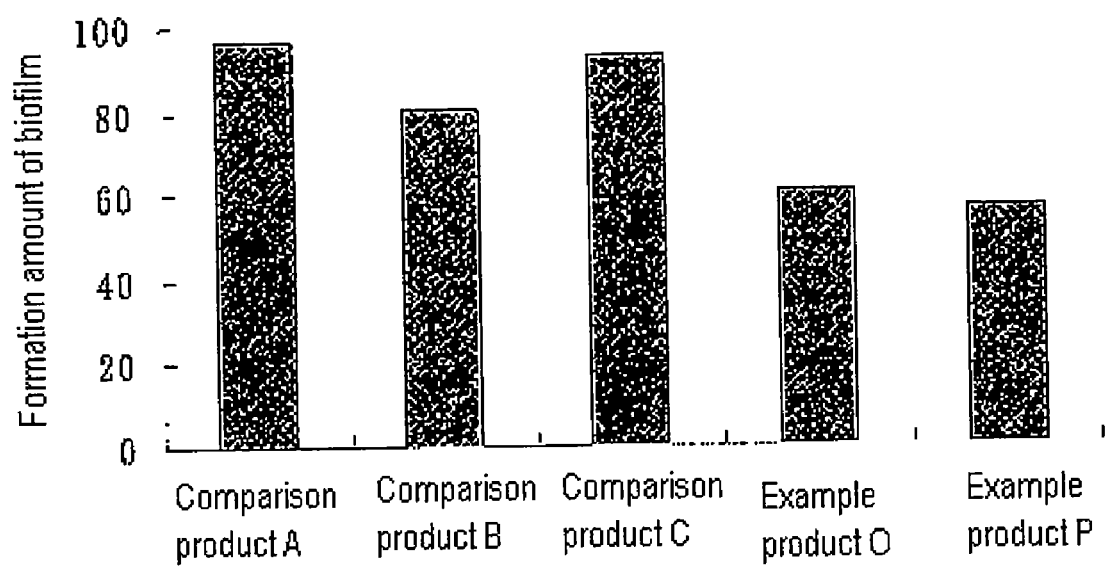

LIQUID COMPOSITIONS FOR THE ORAL CAVITY

FIELD OF THE INVENTION

The present invention relates to a liquid composition for the oral cavity, which is excellent in the adsorption of bactericide onto the teeth and the oral mucosa, barely causes an unpleasant taste, and has good stability.

BACKGROUND OF THE INVENTION

Cationic bactericides such as benzethonium chloride and cetylpyridinium chloride are incorporated in many compositions for the oral cavity because they have high bactericidal activity against oral bacteria, readily adsorb to the surface of the oral tissues such as the teeth and the oral mucosa, and prevent the formation of biofilms such as plaque and tongue coating.

Cationic bactericides, on the other hand, usually have a strong unpleasant taste such as bitterness so that an oil-soluble flavor is used in combination therewith in order to mask such a taste and improve the feeling upon use. When an oil-soluble flavor is incorporated, a solubilizer such as an anionic or nonionic surfactant is used as an essential component, but such a surfactant or an oil-soluble flavor tends to impair the adsorption of the cationic bactericide to the surface of the oral tissues such as the teeth and the oral mucosa. A technology of preparing a composition for the oral cavity without adding thereto an oil-soluble flavor or surfactant is reported (Patent Document 1) as a method of overcoming such an inconvenience, but this technology has problems that because of a water-soluble flavor used instead of the oil-soluble flavor, the resulting composition lacks a cooling sensation and has less freedom of choice in the design of its taste. In addition, the technology of solubilizing an oil-soluble flavor with a small amount of surfactant is proposed (Patent Document 2). Owing to a polyoxyethylene-added nonionic surfactant used in this technology, the adsorption of the cationic bactericide to the surface of the oral tissues such as teeth and oral mucosa is not always sufficient. Further, the technology of adding polyoxyethylene polyoxypropylene glycol which is a nonionic surfactant in order to bring out the effect of the bactericide fully (Patent Document 3) is proposed. This technology however has a problem that owing to the insufficient solubilizing power of the surfactant, the surfactant added in an amount enough to obtain a transparent and stable liquid composition impairs the cooling sensation of the oil-soluble flavor.

[Patent Document 1] JP-A-07-101842
[Patent Document 2] JP-A-2001-302478
[Patent Document 3] JP-A-04-202121

DISCLOSURE OF THE INVENTION

In one aspect of the present invention, there is thus provided a liquid composition for the oral cavity (1), which contains the following components (A), (B), (C) and (D):
(A) an oil-soluble flavor,
(B) a cationic bactericide,
(C) a sugar fatty acid ester, and
(D) one or more compounds selected from the group consisting of polyglycerol fatty acid esters, polyoxyethylene hydrogenated castor oils, and sorbitan fatty acid esters.

In another aspect of the present invention, there is also provided a liquid composition for the oral cavity (2), which contains the following components (A), (B), (E) and (F):
(A) an oil-soluble flavor,
(B) a cationic bactericide,
(E) a polyphosphoric acid or salt thereof, and
(F) a polyglycerol fatty acid ester.

BRIEF DESCRIPTION OF THE DRAWINGS

FIG. 1 is a graph showing the relationship between the adsorption ratio of a bactericide to hydroxyapatite and the concentration of a polyphosphoric acid.

FIG. 2 is a graph showing the effect of pH of the liquid composition for the oral cavity according to the present invention on the adsorption ratio of a bactericide to hydroxyapatite.

FIG. 3 is a graph showing the inhibitory effect of the liquid composition for the oral cavity according to the present invention against the formation of a biofilm.

MODE FOR CARRYING OUT THE INVENTION

The present invention provides a liquid composition for the oral cavity, which contains a cationic bactericide, is excellent in the adsorption of the bactericide to the surface of the oral tissues such as teeth and oral mucosa, and shows good stability over a long period of time.

The present inventors have carried out various investigations on the adsorption, to the teeth and the like, of a cationic bactericide contained in a composition for the oral cavity in the case where the composition contains an oil-soluble flavor for masking an unpleasant taste of the cationic bactericide. As a result, it has been found that although a nonionic surfactant was presumed to reduce the adsorption of a bactericide, use of one or more compounds selected from the group consisting of sugar fatty acid esters, polyglycerol fatty acid esters, polyoxyethylene hydrogenated castor oils, and sorbitan fatty acid esters in combination with the surfactant makes it possible to obtain the liquid composition for the oral cavity (1) showing drastically improved adsorption of the cationic bactericide to the teeth and the like, not having a strong bitter taste, and having good stability.

The present inventors have also found that the liquid composition for the oral cavity (2) having drastically improved adsorption of a cationic bactericide to the surface of the teeth and the like over a wide pH range and having an excellent inhibitory effect against the formation of a biofilm such as plaque and tongue coating is available by incorporating the cationic bactericide with a combination of polyphosphoric acid or salt thereof and a polyglycerol fatty acid ester.

When the liquid composition for the oral cavity according to the present invention is used, the cationic bactericide efficiently adsorbs to the surface of the oral tissues such as teeth and oral mucosa in a large amount and exhibits a strong bactericidal power. The composition can therefore strongly inhibit the formation of a biofilm such as plaque or tongue coating and as a result, is excellent in the effect of preventing troubles in the mouth such as caries, periodontal diseases and bad breath. In addition, the composition is suited for continued use because it does not leave a strong unpleasant taste such as bitterness. Moreover, it has long-term stability.

The liquid composition for the oral cavity (1) containing the components (A), (B), (C) and (D) will be described hereinafter.

The oil-soluble flavor (A) to be added to the liquid composition for the oral cavity (1) according to the present invention is a substance for masking the unpleasant taste of the cationic bactericide such as bitterness and it has a ClogP of from −0.5 to 6, preferably a ClogP of from 0.2 to 5. The term "ClogP" as used herein means a coefficient indicating the affinity of an organic compound for water and 1-octanol. A 1-octanol/water partition coefficient P is the partition equilibrium when a trace amount of the compound is dissolved as a solute in a solvent composed of two liquid phases, that is, 1-octanol and water and it is defined as the ratio of the equilibrium concentrations of the compound in respective solvents. It is usually given in the form of log P which is a logarithm to base 10. The log P values of many compounds have been reported and the log P can be calculated using a program "CLOGP" available from Daylight Chemical Information Systems, Inc. (Daylight CIS) or the like. Many values are listed in the database of Daylight CIS.

The "CLOCP" is obtained using a calculated logP (ClogP) value determined by the fragment approach of Hansch Leo. The fragment approach is based on the chemical structure of a compound, taking the number of atoms and the type of chemical bond into account (cf. A. Leo Comprehensive Medicinal Chemistry, Vol. 4C. Hansch, P. G. Sammens, J. B Taylor and C. A. Ramsden, Eds., P. 295, Pergamon Press, 1990).

This ClogP value is most common and a reliable predicted value at present so that it can be used instead of an actually measured log P value in selecting a compound. In the present invention, an actually measured log P value is used if any and if not, a ClogP value calculated using the program CLOGP v4.01 is used instead.

Examples of the flavor usable as Component (A) include, in addition to synthetic flavors such as menthol, carvone, anethole, eugenol, cineol, thymol, methyl salicylate, pulegone, menthone, pinene, limonene and menthyl acetate, natural essential oils, for example, mint oils such as peppermint oil, spearmint oil and menthol oil, citrus oils such as lemon, orange, grapefruit and lime, herb oils such as eucalyptus, sage, rosemary, thyme, laurel, basil, Japanese basil, bay, estragon, parsley, celery and coriander, and spice oils such as cinnamon, pepper, nutmeg, mace, clove, ginger, cardamom and anise; and fruit flavors such as apple, banana, melon, grape, peach, strawberry, blueberry, raspberry, blackcurrant, litchee, star fruit, passion fruit, plum, pineapple and Muscat. Of these oil soluble flavors, menthol, carvone, peppermint oil, spearmint oil, mint oil, methyl salicylate, cineole, limonene and pinene are even more preferred because they can give a cooling sensation or refreshed feeling to the oral cavity. These oil soluble flavors may be used either singly or in combination of two or more.

Component (A) is added in an amount of preferably from 0.1 to 2 mass %, more preferably from 0.2 to 1 mass %, even more preferably from 0.3 to 0.7 mass % to the liquid composition for the oral cavity (1) according to the present invention in order to achieve the effect of masking the unpleasant taste of the cationic bactericide.

The cationic bactericide (B) adsorbs to the surfaces of the oral tissues such as the surface of the teeth and the oral mucosa (including the gum) and has a bactericidal action against bacteria causing dental caries, periodontal diseases and bad breath. Examples of it include quaternary ammonium compounds and biguanide compounds. Examples of the bactericides belonging to the quaternary ammonium compounds include cetylpyridinium chloride, dequalinium chloride, benzethonium chloride, benzalkonium chloride, alkyldimethylammonium chloride, alkyltrimethylammonium chloride, methylbenzethonium chloride and lauroyl ester of colaminoformylmethylpyridinium chloride. Examples of the bactericides belonging to the biguanide compounds include chlorhexidine and salts thereof, preferably chlorhexidine gluconate and chlorhexidine hydrochloride. As Component (B), these bactericides may be used either singly or in combination of two or more. It is preferred to add Component (B) in an amount of preferably from 0.001 to 0.5 mass %, more preferably from 0.005 to 0.2 mass % to the liquid composition for the oral cavity (1) according to the present invention from the viewpoints of bactericidal action and taste.

The sugar fatty acid ester (C) is a sugar fatty acid ester wherein the sugar has from 16 to 18 carbon atoms, preferably a sugar fatty acid ester wherein the sugar has from 10 to 14 carbon atoms, more preferably a sugar fatty acid ester wherein the sugar has 12 carbon atoms. Specific examples include sucrose fatty acid esters, maltose fatty acid esters and lactose fatty acid esters. These sugar fatty acid esters are effective for drastically improving the adsorption amount of the cationic bactericide to the teeth and the like. The fatty acid moiety of these sugar fatty acid esters is, for example, a saturated or unsaturated fatty acid having from 6 to 24 carbon atoms and specific examples include lauric acid, myristic acid, palmitic acid, oleic acid and stearic acid. Component (C) is added in an amount of preferably from 0.01 to 2 mass %, more preferably from 0.05 to 1 mass %, even more preferably from 0.1 to 0.8 mass % to the liquid composition for the oral cavity (1) according to the present invention from the viewpoints of the above-described adsorption improving effect, stability and taste.

When used in combination with Component (C), the polyglycerol fatty acid ester, polyoxyethylene hydrogenated castor oil and/or sorbitan fatty acid ester (D) are (is) effective for improving the taste and stability. In particular, the polyglycerol fatty acid ester is preferred from the viewpoint of improving the adsorption amount of the cationic bactericide to the teeth and the like. In the polyglycerol fatty acid ester, the degree of condensation of glycerin is preferably from 2 to 20, more preferably from 5 to 12. Examples of the fatty acid moiety include saturated or unsaturated fatty acids having from 6 to 24 carbon atoms. From the viewpoint of stability, lauric acid, myristic acid, palmitic acid and stearic acid are preferable fatty acids. The degree of polymerization of polyoxyethylene of the polyoxyethylene hydrogenated castor oil is preferably from 5 to 120, more preferably from 10 to 100. Examples of the fatty acid moiety of the sorbitan fatty acid ester include saturated or unsaturated fatty acids having from 6 to 24 carbon atoms. From the viewpoint of stability, lauric acid, myristic acid, palmitic acid and stearic acid are preferable fatty acids. These polyglycerol fatty acid esters, polyoxyethylene hydrogenated castor oils and sorbitan fatty acid esters may be used either singly or in combination. Component (D) is added in an amount of preferably from 0.001 to 2 mass %, more preferably from 0.005 to 1 mass %, even more preferably from 0.01 to 0.8 mass % to the liquid composition (1) for the oral cavity according to the present invention from the viewpoints of taste and stability, even more stability. A ratio of Component (C) to Component (D) in terms of mass ratio is preferably from 30:1 to 1:10, more preferably from 10:1 to 1:5 in order to improve the stability and adsorption amount of the cationic bactericide to the teeth and the like.

The liquid composition for the oral cavity (1) according to the present invention preferably contains ethanol further from the standpoint of improving the bactericidal effect and cooling sensation. The content of ethanol in the liquid composition for the oral cavity is preferably from 0.5 to 30 mass %, more preferably from 1 to 20 mass %, even more preferably from 4 to 15 mass %.

The liquid composition for the oral cavity (1) can be free of an anionic surfactant.

The liquid composition for the oral cavity (1) according to the present invention can further contain an anionic surfactant, nonionic surfactant other than Component (C) and Component (D), sugar alcohol, binder, polyol, buffer, another medicinal component, sweetener, water and the like.

Examples of the anionic surfactant include alkyl sulfate ester salts such as sodium lauryl sulfate and sodium myristyl sulfate, N-acylamino acid salts such as lauroylsarcosine sodium; acyl taurine salts such as sodium lauroylmethyltaurine, and fatty acid ester sulfonate salts such as sodium cocoyl ethyl ester sulfonate.

The anionic surfactant is added preferably in an amount of 0.01 mass % or less (from 0 to 0.01 mass %) to the liquid composition for the oral cavity (1) from the standpoints of irritation and adsorption of the cationic bactericide to the teeth and the like.

Examples of the sugar alcohol usable in the present invention include erythritol, xylitol, ribitol, arabitol, galactitol, sorbitol, mannitol, maltitol, palatinit, lactitol, maltotriitol, isomaltotriitol, maltotetraitol, isomaltotetraitol, and reduced malt syrup. Of these, erythritol, xylitol and palatinit are preferred because they can suppress the formation of a biofilm. The total content (mass ratio) of erythritol, xylitol and palatinit is preferably ½ or greater, more preferably ⅔ or greater in the sugar alcohols.

These sugar alcohols are incorporated in the liquid composition for the oral cavity (1) according to the present invention in an amount of preferably from 4 to 50 mass %, more preferably from 5 to 35 mass %, even more preferably from 6 to 20 mass % in order to achieve a pleasant cooling sensation and unpleasant taste/unpleasant odor preventing effects.

Examples of the binder include cellulose derivatives such as sodium carboxymethylcellulose and hydroxyethyl cellulose, alginic acid derivatives such as sodium alginate and propylene glycol alginate, gums such as carrageenan, xanthan gum, Duran gum, tragacanth gum, and karaya gum, synthetic binders such as polyvinyl alcohol, sodium polyacrylate, and carboxyvinyl polymer, inorganic binders such as silica gel, bee gum, and laponite, and starch decomposition products such as dextrin and reduced dextrin. These binders may be used either singly or in combination of two or more.

Examples of the polyol include propylene glycol, glycerin, and polyethylene glycol. Examples of the buffer include citric acid and salts thereof, malic acid and salts thereof, and phosphoric acid and salts thereof. Examples of the sweetener include sodium saccharin, acesulfame potassium, stevioside, neohesperidyl dihydrochalcone, glycyrrhizin, perillartine, thaumatin, aspartyl-phenylalanyl methyl ester, and sucralose. Examples of another medicinal component include plasmin antagonists such as tranexamic acid and epsilon-amino-caproic acid, vitamins such as ascorbic acid and tocopherol ester, glycyrrhizin salts, allantoins, plant extracts such as cork tree bark, Scutellariae Radix, chamomile, rhatany, and mirra, enzymes such as dextranase, mutanase and lysozyme chloride, alkali metal monofluorophosphates such as sodium monofluorophosphate, fluorides such as sodium fluoride and stannous fluoride, salts such as sodium chloride, potassium nitrate, carbonates, bicarbonates, and sesquicarbonates, sodium copper chlorophyllin, copper gluconate, zinc chloride, zeolite, water-soluble inorganic phosphoric acid compounds, and aluminum lactate. One or more of them is usable.

The liquid composition for the oral cavity (2) containing the components (A), (B), (E) and (F) will next be described.

In the present invention, the oil soluble flavor (A) and the cationic bactericide (B) employed for this composition and contents of them are similar to those employed in the liquid composition for the oral cavity (1).

The polyphosphoric acid or salt thereof (E) is effective for improving the adsorption of the cationic bactericide to the surface of the teeth and the like. Examples of the polyphosphoric acid include linear polyphosphoric acids such as pyrophosphoric acid, tripolyphosphoric acid, tetrapolyphosphoric acid and metaphosphoric acid; and cyclic polyphosphoric acids such as trimetaphosphoric acid, tetrametaphosphoric acid and hexametaphosphoric acid. Examples of the salt of a polyphosphoric acid include alkali metal salts such as sodium salt and potassium salt, and ammonium salts. Of these, alkali metal salts are preferred because of their ease in handling. Component (E) is incorporated in the liquid composition for the oral cavity (2) according to the present invention in an amount of preferably from 0.001 to 1 mass %, more preferably from 0.005 to 0.5 mass %, even more preferably from 0.01 to 0.2 mass % from the standpoint of an adsorption improving effect.

The polyglycerol fatty acid ester (F) is effective for improving the adsorption of the cationic bactericide to the surface of the teeth or the like over a wide pH range when used in combination with Component (E). The degree of the condensation of glycerin of the polyglycerol fatty acid ester is preferably from 2 to 20, more preferably from 5 to 12. Examples of the fatty acid moiety include saturated or unsaturated fatty acids having from 6 to 24 carbon atoms. From the viewpoint of stability, lauric acid, myristic acid, palmitic acid and stearic acid are preferred. Component (F) is incorporated in the liquid composition for the oral cavity (2) according to the present invention in an amount of preferably from 0.01 to 2 mass %, more preferably from 0.05 to 1 mass %, even more preferably from 0.1 to 0.8 mass % from the viewpoint of an adsorption improving effect over a wide pH range.

It is possible to add, to the liquid composition for the oral cavity (2) according to the present invention, a nonionic surfactant other than the polyglycerol fatty acid ester (F) and examples of such a nonionic surfactant include sugar fatty acid esters, polyoxyethylene hydrogenated castor oils, sorbitan fatty acid esters, polyoxyethylene-polyoxypropylene block copolymer type nonionic surfactants, fatty acid alkanolamides, polyoxyethylene fatty acid esters, fatty acid monoglycerides, and polyoxyethylene alkyl ethers. Use of a sucrose fatty acid ester, maltose fatty acid ester or lactose fatty acid ester is preferred because it is effective for improving the adsorption of the cationic bactericide to the surface of teeth or the like over a wide pH range. Examples of the fatty acid moiety of the above-described sugar fatty acid ester include saturated or unsaturated fatty acids having from 6 to 24 carbon atoms. Specific examples include lauric acid, myristic acid, palmitic acid, oleic acid and stearic acid.

The nonionic surfactant other than the polyglycerol fatty acid ester is incorporated in the liquid composition for the oral cavity (2) according to the present invention in an amount of preferably from 0.001 to 2 mass %, more preferably from 0.005 to 1 mass %, even more preferably from 0.01 to 0.8 mass % from the viewpoint of the above-described adsorption improving effect.

The liquid composition for the oral cavity (2) according to the present invention preferably contains ethanol further from the standpoint of improving the bactericidal effect and cooling sensation. The content of ethanol in the liquid composition for the oral cavity (2) is preferably from 0.5 to 30 mass %, more preferably from 1 to 20 mass %, even more preferably from 4 to 15 mass %.

The liquid composition for the oral cavity (2) can be free of an anionic surfactant.

The liquid composition for the oral cavity (2) according to the present invention can further contain an anionic surfactant, oil soluble flavor, sugar alcohol, binder, polyol, buffer, another medicinal component, sweetener, water and the like.

Examples of these components and amount thereof are similar to those employed in the liquid composition for the oral cavity (1).

The liquid compositions for the oral cavity according to the present invention can be used as dental rinse, mouthwash, mouth spray, gargle, or the like.

EXAMPLES

Mouthwashes as shown in Tables 1 and 2 were prepared and tests on stability, taste and adsorption of a bactericide to teeth were performed in the below-described manners, respectively. Each mouthwash was prepared by dissolving a flavor such as menthol in water containing a surfactant and then mixing the resulting solution with an aqueous erythritol solution.

[Stability Test]

After preparation of each mouthwash, it was allowed to stand at 50° C. for 2 weeks. The appearance of the resulting liquid was evaluated based on the following criteria:

Criteria
A: The liquid is transparent.
B: The liquid is slightly transparent.
C: The liquid is not transparent but no separation is observed.
D: Separation of the liquid is observed.

[Bitterness Test]

Bitterness which had remained in the mouth after gargling with 10 mL of the mouthwash for 30 seconds and spitting it out was judged based on the following criteria:

Criteria:
A: No bitterness remained.
B: Slight bitterness remained.
C: Bitterness remained.
D: Severe bitterness remained.

[Adsorption Test of Bactericide]

As a model of teeth, hydroxyapatite (HA) powder (which will hereinafter be abbreviated as "HA"; product of Taihei Chemical) which is a main component of enamel was used. After dipping 10 mg of HA in 1 mL of each mouthwash shown in Table 1 and Table 2 for 30 seconds, it was washed with 2 mL of ion exchange water. The bactericide adsorbed to HA was extracted with a 65% acetonitrile solution and was quantitatively analyzed by high performance liquid chromatography (ODS column: "Superspher 100" (product of Kanto Chemical), flow rate: 1 mL/min, measurement wavelength: 210 nm), whereby an adsorption amount was determined.

TABLE 1

[mass %]

| | Comparative Examples | | | | | | | |
|---|---|---|---|---|---|---|---|---|
| | 1 | 2 | 3 | 4 | 5 | 6 | 7 | 8 |
| Polyoxyethylene (60) hydrogenated castor oil | | 0.4 | | | | | 0.2 | |
| Sucrose myristate ester | | | 0.4 | | | 0.4 | | |
| Polyglycerol myristate ester | | | | 0.4 | | | 0.1 | 0.5 |
| Sorbitan stearate ester | | | | | 0.4 | | | 0.1 |
| Benzethonium chloride | 0.01 | 0.01 | 0.01 | 0.01 | 0.01 | 0.01 | 0.01 | 0.01 |
| Menthol | | 0.2 | 0.2 | 0.2 | 0.2 | 0.4 | 0.2 | 0.2 |
| Cineol | | 0.01 | 0.01 | 0.01 | 0.01 | 0.02 | 0.01 | 0.01 |
| Spice oil (clove, ginger) | | 0.15 | 0.15 | 0.15 | 0.15 | 0.2 | 0.15 | 0.15 |
| Ethanol | 10 | 10 | 10 | 10 | 10 | 10 | 10 | 10 |
| Glycerin | 3 | 3 | 3 | 3 | 3 | 3 | 3 | 3 |
| Erythritol | 10 | 10 | 10 | 10 | 10 | 10 | 10 | 10 |
| Saccharin sodium | 0.01 | 0.01 | 0.01 | 0.01 | 0.01 | 0.01 | 0.01 | 0.01 |
| Water | Balance | Balance | Balance | Balance | Balance | Balance | Balance | Balance |
| Total | 100 | 100 | 100 | 100 | 100 | 100 | 100 | 100 |
| Results of stability test | A | A | C | D | B | C | A | A |
| Results of taste test | D | C | C | B | C | C | B | B |
| Results of bactericide adsorption test (ng/mg HA) | 23 | 12 | 648 | 295 | 8 | 358 | 21 | 28 |

TABLE 2

[mass %]

| | Examples | | | | | |
|---|---|---|---|---|---|---|
| | 1 | 2 | 3 | 4 | 5 | 6 |
| Polyoxyethylene (60) hydrogenated castor oil | 0.3 | | | | 0.2 | |
| Sucrose myristate ester | 0.3 | 0.1 | 0.3 | 0.3 | 0.2 | 0.1 |
| Polyglycerol myristate ester | | 0.2 | 0.3 | | 0.2 | 0.2 |
| Sorbitan stearate ester | | | | 0.01 | | |
| Benzethonium chloride | 0.01 | 0.01 | 0.01 | 0.01 | 0.01 | 0.01 |
| Menthol | 0.2 | 0.2 | 0.2 | 0.4 | 0.4 | 0.4 |
| Cineol | 0.01 | 0.01 | 0.01 | 0.02 | 0.02 | 0.02 |
| Spice oil (clove, ginger) | 0.15 | 0.15 | 0.15 | 0.2 | 0.2 | 0.2 |
| Ethanol | 10 | 10 | 10 | 10 | 10 | 10 |
| Glycerin | 3 | 3 | 3 | 3 | 3 | 3 |
| Erythritol | 10 | 10 | 10 | 10 | 10 | 10 |
| Saccharin sodium | 0.01 | 0.01 | 0.01 | 0.01 | 0.01 | 0.01 |

TABLE 2-continued

|  | Examples [mass %] | | | | | |
|---|---|---|---|---|---|---|
|  | 1 | 2 | 3 | 4 | 5 | 6 |
| Water | Balance | Balance | Balance | Balance | Balance | Balance |
| Total | 100 | 100 | 100 | 100 | 100 | 100 |
| Results of stability test | A | A | A | B | A | B |
| Results of taste test | B | A | A | B | B | B |
| Results of bactericide adsorption test (ng/mg HA) | 481 | 724 | 630 | 422 | 388 | 520 |

Polyoxyethylene hydrogenated castor oil: polyoxyethylene (60) hydrogenated castor oil
Sugar fatty acid ester: sucrose myristate ester
Polyglycerol fatty acid ester: polyglycerol myristate ester (degree of condensation: 10)
Sorbitan fatty acid ester: sorbitan stearate ester
Flavor: menthol+cineol+spice oil It has been found from the results shown in Table 1 and Table 2, addition of a sugar fatty acid ester to a reaction system containing a cationic bactericide and an oil-soluble flavor causes a drastic improvement in the adsorption of the bactericide. Such an adsorption improving effect is specific to the sugar fatty acid ester. By adding the polyglycerol fatty acid ester, polyoxyethylene hydrogenated castor oil or sorbitan fatty acid ester to the reaction system, a mouthwash excellent in the adsorption of the bactericide, taste of the composition and stability can be prepared.

Example 7

Adsorption Test of Cationic Bactericide to Teeth

Hydroxyapatite (HA) powder (which will hereinafter be abbreviated as "HA", product of Taihei Chemical) which was a main component of enamel was used as the model of teeth. After dipping 10 mg of HA in 1 mL of each mouthwash shown in Table 3 and Table 4 for 30 seconds, it was washed with 2 mL of ion exchange water. The bactericide adsorbed to HA was extracted with a 65% acetonitrile solution and was quantitatively analyzed by high performance liquid chromatography (ODS column: "Superspher 100" (product of Kanto Chemical), flow rate: 1 mL/min, measurement wavelength: 210 nm), whereby an adsorption amount was determined. Each mouthwash shown in Table 3 was prepared by dissolving the flavor in an aqueous solution containing a surfactant and then mixing the resulting solution with an aqueous erythritol solution.

TABLE 3

|  | Comparison product | Example products | | | | |
|---|---|---|---|---|---|---|
|  |  | A | B | C | D | E |
| Polyglycerol myristate ester | 0.6 | 0.6 | 0.6 | 0.6 | 0.6 | 0.6 |
| Ethanol | 8 | 8 | 8 | 8 | 8 | 8 |
| Flavor | 0.2 | 0.2 | 0.2 | 0.2 | 0.2 | 0.2 |
| Benzethonium chloride | 0.01 | 0.01 | 0.01 | 0.01 | 0.01 | 0.01 |
| Erythritol | 7 | 7 | 7 | 7 | 7 | 7 |
| Na pyrophosphate | 0 | 0.01 | 0.02 | 0.04 | 0.08 | 0.2 |
| Water | Balance | Balance | Balance | Balance | Balance | Balance |
| Total (mass %) | 100 | 100 | 100 | 100 | 100 | 100 |

TABLE 4

|  | Example products | | | | | | | |
|---|---|---|---|---|---|---|---|---|
|  | G | H | I | J | K | L | M | N |
| Sucrose myristate ester | 0.3 | 0.3 | 0.3 | 0.3 | 0.3 | 0.3 | 0.3 | 0.3 |
| Polyglycerol myristate ester | 0.4 | 0.4 | 0.4 | 0.4 | 0.4 | 0.4 | 0.4 | 0.4 |
| Ethanol | 6 | 6 | 6 | 6 | 6 | 6 | 6 | 6 |
| Flavor | 0.2 | 0.2 | 0.2 | 0.2 | 0.2 | 0.2 | 0.2 | 0.2 |
| Benzethonium chloride | 0.01 | 0.01 | 0.01 | 0.01 | 0.01 | 0.01 | 0.01 | 0.01 |
| Glycerin | 3 | 3 | 3 | 3 | 3 | 3 | 3 | 3 |
| Na pyrophosphate | 0.02 | 0.02 | 0.02 | 0.02 | 0.02 | 0.02 | 0.02 | 0.02 |
| Water | Balance | Balance | Balance | Balance | Balance | Balance | Balance | Balance |
| Total (mass %) | 100 | 100 | 100 | 100 | 100 | 100 | 100 | 100 |
| Final pH adjusted with phosphate buffer | 5 | 6 | 7 | 8 |  |  |  |  |
| Final pH adjusted with citrate buffer |  |  |  |  | 5 | 6 | 7 | 8 |

Flavor in Table 3 and Table 4
Flavor: 20 mass % of menthol+5 mass % of cineol+75 mass % of herb oil Supposing that the adsorption amount of the bactericide to HA after treatment with the comparison product free of sodium pyrophosphate as shown in Table 3 was 100, an adsorption ratio of the bactericide after treatment with each of Example products A to E was calculated. As a result, as illustrated in FIG. 1, the adsorption amount of the bactericide to HA rose with an increase in the content of a pyrophosphate and the adsorption ratio became constant when the content of pyrophosphoric acid was 0.04 mass % or greater.

In addition, the adsorption amounts of the bactericide after treatment with mouthwashes adjusted to a final pH of from 5 to 8 with a phosphate buffer system and a citrate buffer system (phosphate buffer system mouthwashes: Example products G to J, citrate buffer system mouthwashes: Example products K to N), respectively were measured and a ratio of the adsorption amount of the bactericide was calculated based on the adsorption amount (100%) of the bactericide after treatment with the comparison product shown in Table 3. As a result, as shown in FIG. 2, no significant difference in the adsorption amount of the bactericide to HA due to a pH change was observed in either buffer system.

Example 8

Biofilm Formation Inhibition Test by the Culture Method

As a model of teeth, a pellet plate obtained by compressing hydroxyapatite powder, main component of enamel, into a flat plate having a diameter of about 8 mm (which plate will hereinafter be abbreviated as HAP) was used. After preparation of each mouthwash shown in Table 5, HAP treated at 37° C. for 90 minutes with the saliva collected from a human donor was dipped for 30 seconds in 10 mL of each mouthwash. The HAP was washed with 10 mL of ion exchange water and then, dipped in a culture solution obtained by adding sucrose to the saliva collected from a human donor, and cultivated at 37° C. for 4 days under anaerobic conditions. After cultivation, the biofilm attached on the surface of the HAP was dyed with a plaque dyeing solution and the dyed area was digitalized by image processing (average after color separation in RBG color mode, Measuring instrument VH-7000 (product of KEYENCE), analysis software: WIN-ROOF (product of Mitani Corp)). The formation amount of the biofilm was calculated based on the amount (100%) of the biofilm formed on the HAP surface when treated with ion exchange water instead of a mouthwash.

TABLE 5

|  | Comparison products | | | Example products | |
| --- | --- | --- | --- | --- | --- |
|  | A | B | C | O | P |
| Sucrose laurate ester | 0.2 | 0.2 | 0.2 | 0.2 | 0.2 |
| Polyglycerol myristate ester | 0.4 | 0.4 | 0.4 | 0.4 | 0.4 |
| Ethanol | 10 | 10 | 10 | 10 | 10 |
| Flavor | 0.2 | 0.2 | 0.2 | 0.2 | 0.2 |
| Benzethonium chloride |  | 0.01 |  | 0.01 | 0.01 |
| Sorbitol | 7 | 7 | 7 | 7 | 7 |
| Malic acid |  |  | Trace | Trace | Trace |
| Na tripolyphosphate |  |  | 0.02 | 0.02 | 0.02 |
| Water | Balance | Balance | Balance | Balance | Balance |
| Total amount (mass %) | 100 | 100 | 100 | 100 | 100 |
| Final pH | 6.4 | 6.4 | 6.4 | 6.4 | 8.0 |

Flavor: 20 mass % of menthol+5 mass % of cineol+75 mass % of herb oil

As illustrated in FIG. 3, the treatment with Comparison product A free of a bactericide and tripolyphosphate and the treatment with Comparison product C containing a tripolyphosphate but free of a bactericide did not show any biofilm formation inhibition effect. The treatment with Comparison product B containing a bactericide but not a tripolyphosphate, on the other hand, inhibited biofilm formation by about 20%. The treatment with each of Example products O and P containing both a bactericide and a tripolyphosphate inhibited biofilm formation by about 40% or greater. The effect was brought about by the cationic bactericide adsorbed efficiently to the surface of HAP owing to the addition of a tripolyphosphate and polyglycerol fatty acid ester.

The invention claimed is:

1. A liquid composition for the oral cavity, comprising the following components (A), (B), (E) and (F):
    (A) an oil-soluble flavor,
    (B) a cationic bactericide,
    (E) 0.005 to 0.5 mass % of a polyphosphoric acid or salt thereof, and
    (F) 0.01 to 2 mass % of a polyglycerol fatty acid ester in which the degree of condensation of glycerol is from 5 to 12, and the fatty acid is selected from the group consisting of lauric acid, myristic acid, palmitic acid and stearic acid, wherein said cationic bactericide is a quaternary ammonium compound or a biguanide compound.

2. The liquid composition for the oral cavity according to claim 1, further comprising ethanol.

3. The liquid composition for the oral cavity according to claim 1, further comprising one or more sugar alcohol compounds selected from the group consisting of erythritol, xylitol and ribitol, arabitol, galactitol, sorbitol, mannitol, maltitol, palatinit, lactitol, maltotriitol, isomaltotriitol, maltotetraitol, isomaltotetraitol and reduced malt syrup.

4. The liquid composition for the oral cavity according to claim 3, wherein the total content (mass ratio) of said erythritol, xylitol and palatinit is ½ or greater of the total sugar alcohol content in said composition.

5. The liquid composition for the oral cavity according to claim 1 or claim 2, which further comprises a nonionic surfactant other than said component (F).

6. The liquid composition for the oral cavity according to claim 1 or claim 2, which contains an anionic surfactant.

7. The liquid composition for the oral cavity according to claim 6, wherein said anionic surfactant is present in an amount of 0.01 mass % or less.

8. The liquid composition for the oral cavity according to claim 2, further comprising one or more sugar alcohol compounds selected from the group consisting of erythritol, xylitol and palatinit.

9. The liquid composition for the oral cavity according to claim 5, further comprising one or more compounds selected from the group consisting of erythritol, xylitol and palatinit.

10. The liquid composition according to claim 1, wherein said oil-soluble flavor is a mint oil, an herb oil, a spice oil, a fruit flavor or a synthetic flavor, wherein said synthetic flavor is selected from the group consisting of menthol, carvone, anethole, eugenol, cineol, thymol, methyl salicylate, pulegone, menthone, pinene, limonene and menthyl acetate.

11. The liquid composition according to claim 1, wherein said polyphosphoric acid is pyrophosphoric acid, tripolyphosphoric acid, tetrapolyphosphoric acid, metaphosphoric acid, trimetaphosphoric acid, tetrametaphosphoric acid or mexametaphosphoric acid.

12. A liquid composition for the oral cavity, comprising the following components:
   (A) an oil-soluble flavor in an amount of 0.1 to 2 mass %,
   (B) a cationic bactericide in an amount of 0.001 to 0.5 mass %,
   (E) a polyphosphoric acid or salt thereof in an amount of 0.005 to 0.5 mass %, and
   (F) a polyglycerol fatty acid ester in an amount of 0.01 to 2 mass % in which the degree of condensation of glycerol is from 5 to 12, and the fatty acid is selected from the group consisting of lauric acid, myristic acid, palmitic acid and stearic acid,
   wherein said cationic bactericide is a quaternary ammonium compound or a biguanide compound.

13. The liquid composition for the oral cavity according to claim 12, wherein the mass ratio of component (E) to component (F) is 0.01:0.6 to 0.2:0.6.

14. The liquid composition for the oral cavity according claim 12, further comprising one or more sugar alcohol compounds selected from the group consisting of erythritol, xylitol, ribitol, arabitol, galactitol, sorbitol, mannitol, maltitol, palatinit, lactitol, maltotriitol, isomaltotriitol, maltotetraitol, isomaltotetraitol and reduced malt syrup.

15. The liquid composition for the oral cavity according to claim 14, wherein the total, content (mass ratio) of said erythritol, xylitol and palatinit is ½ or greater of the total sugar alcohol content in said composition.

16. The liquid composition for the oral cavity according to claim 1, wherein said composition is a dental rinse, mouthwash, mouth spray or gargle.

17. The liquid composition for the oral cavity according to claim 5, wherein said composition further comprises a sugar fatty acid ester.

18. The liquid composition according to claim 1, wherein said cationic bactericide is said quaternary ammonium compound.

19. The liquid composition for the oral cavity according to claim 18, wherein said quaternary ammonium compound is selected from the group consisting of cetylpyridinium chloride, dequalinim chloride, benzethonium chloride, benzalkonium chloride, alkyldimethylammonium chloride, alkylrimethylammonium chloride, methylbenzethonium chloride and the lauroyl ester of colaminoformylmethylpyridinium chloride.

20. The liquid composition according to claim 1, wherein said cationic bactericide is said biguanide compound.

21. The liquid composition for the oral cavity according to claim 19, wherein said biguanide compound is selected from the group consisting of chlorhexidine and a salt thereof.

22. The liquid composition according to claim 12 or 21, wherein polyphosphoric acid or salt thereof is present in the amount of 0.005 to 0.08 mass %.

23. The liquid composition according to claim 12 or 21, further comprising 0.8 to 0.01 mass % of a nonionic surfactant other than said polyglycerol fatty acid ester.

* * * * *

UNITED STATES PATENT AND TRADEMARK OFFICE
CERTIFICATE OF CORRECTION

PATENT NO. : 8,236,286 B2  
APPLICATION NO. : 11/576858  
DATED : August 7, 2012  
INVENTOR(S) : Yano et al.

Page 1 of 1

It is certified that error appears in the above-identified patent and that said Letters Patent is hereby corrected as shown below:

Column 12
Lines 45-46, Claim 3, please replace "xylitol and ribitol" with --xylitol, ribitol--.

Column 14
Lines 18-19, Claim 19, please replace "alkylrimethylammonium chloride" with --alkyltrimethylammonium chloride--.

Signed and Sealed this  
Twenty-second Day of January, 2013

David J. Kappos  
*Director of the United States Patent and Trademark Office*